United States Patent
Marano-Ford et al.

(10) Patent No.: US 7,128,730 B2
(45) Date of Patent: *Oct. 31, 2006

(54) APPARATUS FOR DELIVERY OF THERAPEUTIC AND/OR DIAGNOSTIC AGENTS

(75) Inventors: April Marano-Ford, Manhattan Beach, CA (US); Susan McConnell-Montalvo, Woodland Hills, CA (US); Jeffrey F. Field, Camarillo, CA (US)

(73) Assignee: Medsolve Technologies, Inc., Manhattan Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/300,005

(22) Filed: Dec. 13, 2005

(65) Prior Publication Data

US 2006/0095003 A1    May 4, 2006

Related U.S. Application Data

(62) Division of application No. 11/040,590, filed on Jan. 20, 2005, now Pat. No. 6,991,620, and a division of application No. 11/040,550, filed on Jan. 20, 2005, now Pat. No. 7,022,108, and a division of application No. 11/040,544, filed on Jan. 20, 2005, now Pat. No. 6,991,619, which is a division of application No. 10/435,620, filed on May 9, 2003, now Pat. No. 6,926,694.

(51) Int. Cl.
*A61M 5/178* (2006.01)
(52) U.S. Cl. .................. 604/167.05; 604/539
(58) Field of Classification Search ............... 604/115, 604/117, 134–136, 156, 157, 264, 523, 164.11, 604/165.04, 167.01, 167.03, 167.04, 167.05, 604/167.06, 533, 534, 539; 606/182–184
See application file for complete search history.

(56) References Cited

U.S. PATENT DOCUMENTS

| | | | |
|---|---|---|---|
| 4,755,173 A | 7/1988 | Konopka et al. | 604/167 |
| 4,842,591 A | 6/1989 | Luther | 604/283 |
| 5,176,662 A | 1/1993 | Bartholomew et al. | 604/283 |
| 5,470,319 A | 11/1995 | Mayer | 604/167 |
| 5,522,803 A | 6/1996 | Teissen-Simony | 604/177 |
| 5,545,143 A | 8/1996 | Fischell | 604/180 |
| 5,616,130 A | 4/1997 | Mayer | 604/167 |
| 5,851,197 A | 12/1998 | Marano et al. | 604/135 |
| 5,968,011 A | 10/1999 | Larsen et al. | 604/93 |

(Continued)

*Primary Examiner*—Sharon Kennedy
(74) *Attorney, Agent, or Firm*—Connolly Bove Lodge & Hutz LLP

(57) ABSTRACT

A system for delivery of therapeutic and/or diagnostic agents into a living body includes a port assembly having a cannula extending from the mounting side, a port opening away from the mounting side and a resilient barrier between the port and the cannula. An access hub includes a connector positionable at the port for opening the resilient barrier. The access hub is movable in the port assembly, is engaged therewith through a resilient ring coupling and forms a seal with the resilient barrier, reducing the amount of volume to be primed. Inserters, both disposable and reusable, include the cannula insertion member as part of the assembly. A spring loaded port driver is operatively mounted within the housing with movement controlled by a latch. The driver includes a seat for receipt of a port assembly. The cannula insertion member is nonremovably fixed in a socket in the port driver in the disposable assembly. In the reusable inserter, the cannula insertion member is slidably mounted within a socket associated with the latch. Slidable movement is limited by locking shoulders. The socket is split and may be splayed to release the cannula insertion member following use.

7 Claims, 9 Drawing Sheets

U.S. PATENT DOCUMENTS

| | | | |
|---|---|---|---|
| 5,980,506 A | 11/1999 | Mathiasen | 604/535 |
| 6,056,718 A | 5/2000 | Funderbruk et al. | 604/93 |
| 6,086,575 A | 7/2000 | Mejslov | 604/533 |
| 6,093,172 A | 7/2000 | Funderburk et al. | 604/135 |
| 6,123,690 A | 9/2000 | Mejslov | 604/283 |
| 6,293,925 B1 | 9/2001 | Safabash et al. | 604/136 |
| 6,488,663 B1 | 12/2002 | Steg | 604/164.08 |
| 6,520,938 B1 | 2/2003 | Funderburk et al. | 604/164.08 |
| 6,685,674 B1 | 2/2004 | Douglas et al. | 604/167.05 |
| 6,736,797 B1 | 5/2004 | Larsen et al. | |
| 6,830,562 B1 | 12/2004 | Mogensen et al. | 604/164.12 |

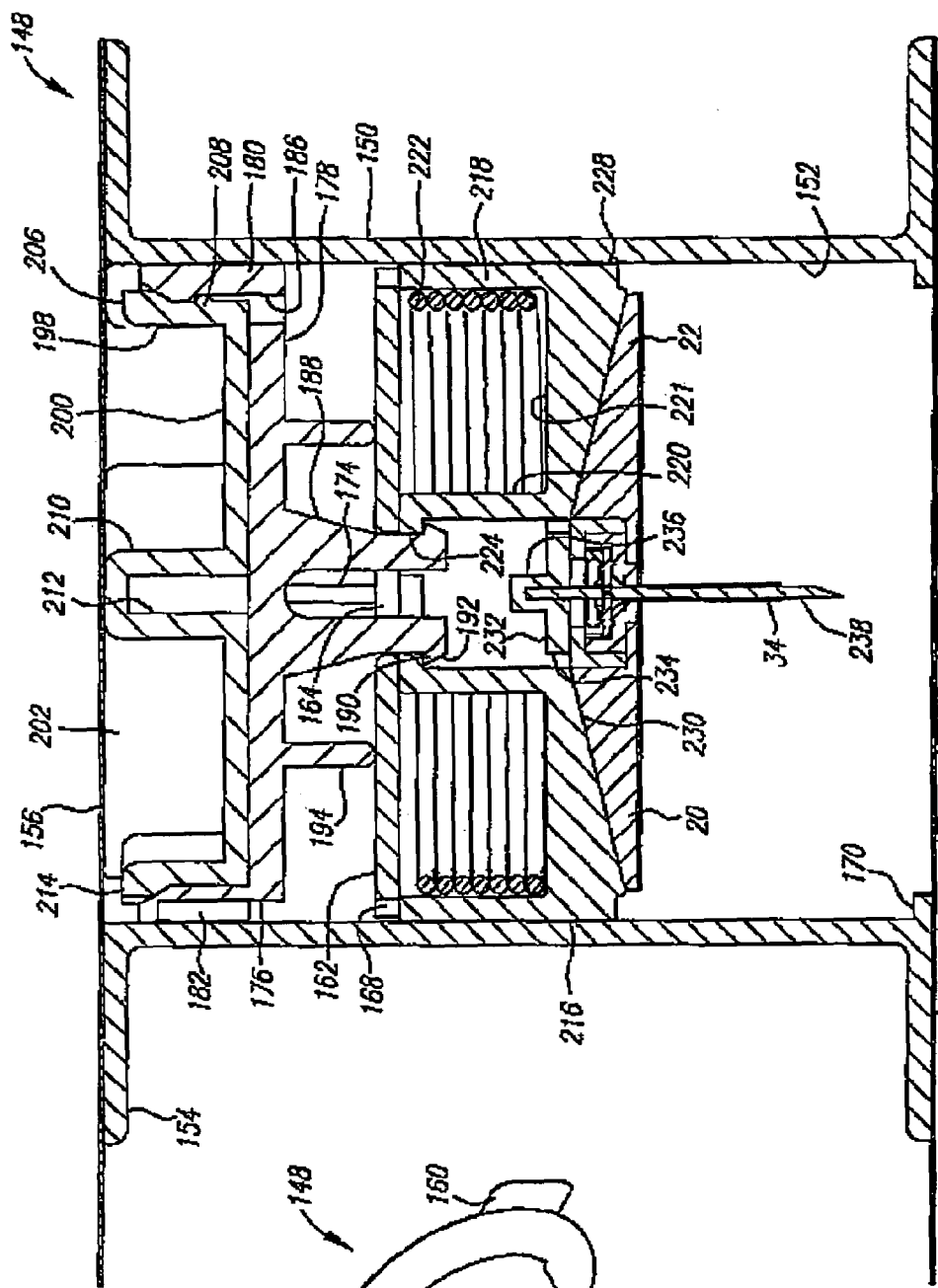

APPARATUS FOR DELIVERY OF
THERAPEUTIC AND/OR DIAGNOSTIC
AGENTS

This is a divisional application of U.S. patent applications Ser. No. 11/040,590 filed Jan. 20, 2005, now U.S. Pat. No. 6,991,620, Ser. No. 11/040,550filed Jan. 20, 2005, now U.S. Pat. No. 7,022,108; and Ser. No. 11/040,544 filed Jan. 20, 2005, now U.S. Pat. No. 6,991,619; which are divisional applications of Ser. No. 10/435,620 filed May 9, 2003, now U.S. Pat. No. 6,926,694, issued Aug. 9, 2005, all to the same inventors, the disclosures of which are incorporated herein by reference.

BACKGROUND OF THE INVENTION

The field of the present invention is devices for the delivery or placement of therapeutic or diagnostic agents into a living body.

Some medical procedures employ the infusion of therapeutic agents into living bodies over periods of time, making a syringe inconvenient and/or inappropriate. Such procedures have been used for the infusion of insulin, for example. In other cases, monitoring of internal body conditions with small sensors or other devices also makes syringes and like devices inappropriate for continuing access to subcutaneous tissue. To provide access in either circumstance, ports have been devised which provide support for a flexible cannula implanted in the body. Ports typically provide a housing which has a mounting side that is held by tape, dressings or direct adhesive against the body. A flexible cannula extends from the housing into the body.

Ports used for infusion may be employed in combination with a delivery tube extending to the housing of the port and in communication with the cannula as a complete infusion set. The delivery tube of such an infusion set is in communication with the flexible cannula through an infusion fluid chamber in the port to deliver therapeutic agents. Diagnostic agents such as biosensors may be delivered in like manner.

To place such ports or infusion sets including such ports, insertion sets have been used. An insertion set typically includes the port and necessarily includes a rigid sharp such as a needle which is placed through the flexible cannula for insertion into the body. The needle typically extends through a resilient barrier such as a resealable resilient mass, through a chamber and then axially through the cannula. Once the cannula has been positioned in the body, the port is positioned and the needle can be withdrawn. The resealing of the mass as the needle is withdrawn prevents fluid from leaking from the port while remaining in position at the site. Once the port has been placed with the flexible cannula extending into the body, the agent or agents can be delivered.

A first type of insertion set includes an infusion set having the port and a delivery tube in communication with the cannula. The insertion set needle accesses the housing through a different path than the delivery tube. The seal is typically bypassed by the delivery tube in this instance. Alternatively, the insertion set is used with a port rather than a complete infusion set. The delivery tube is placed after insertion of the port to complete an infusion set. The same path is used for the insertion needle as part of the insertion set as is used for communicating the tube of the infusion set with the cannula. In this latter case, the delivery tube is associated with a hub which includes a member able to pierce a resealable resilient mass for communication between the delivery tube and the cannula once the insertion set has been disassembled through retraction of the needle.

Mechanisms referred to as inserters have been devised to rapidly insert the needle and cannula into the body at the site. For the infusion of insulin in particular, diabetics self medicate. Consequently, they, a family member or other care provider places the port for infusion. This can be emotionally and physically difficult when repeated infusions are required over long periods of time. Inserters alleviate this burden somewhat by making the placement of the needle automatic and quick. Further, pressure by the inserter about the targeted site reduces the sensation of pain.

Inserters typically include a housing with a driver slidable in the housing. The driver includes a socket to receive the insertion set. A spring is operatively placed between the housing and the driver to advance rapidly an insertion set positioned in the socket. A latch then controls the advancement of the driver. One complete system including an infusion port, an insertion set having the infusion port and an insertion needle, and an inserter is illustrated in U.S. Pat. No. 6,293,925.

SUMMARY OF THE INVENTION

The present invention is directed to a system for the delivery of therapeutic and/or diagnostic agents and components therefore.

In a first separate aspect of the present invention, a port assembly includes a base having a mounting side with a port opening away from the mounting side and a cannula extending from the mounting side. A resilient barrier with a hole therethrough is located between the port and the cannula to control communication therebetween. An access hub includes a connector which can be positioned in the port such that the hole in the resilient barrier is closed with the connector displaced from being positioned in the port and open with the connector fully positioned in the port.

In a second separate aspect of the present invention, the first separate aspect may additionally include such features as a circular bead about the hole on the resilient barrier, a protrusion on the resilient barrier which is in interference with the connector when placed fully in the port and a resilient element in the port biasing the connector toward the resilient barrier with the connector fully positioned in the port.

In a third separate aspect of the present invention, any of the foregoing aspects are employed in combination to greater advantage.

Accordingly, it is an object of the present invention to provide an improved system for delivery of therapeutic and/or diagnostic agents into a living body. Other and further objects and advantages will appear hereinafter.

BRIEF DESCRIPTION OF THE DRAWINGS

FIG. 11 is a perspective view of a port inserter.

FIG. 12 is a cross-sectional view of the port inserter of FIG. 11 taken through the axis of the port inserter.

DETAILED DESCRIPTION OF THE PREFERRED EMBODIMENTS

Figure 1:
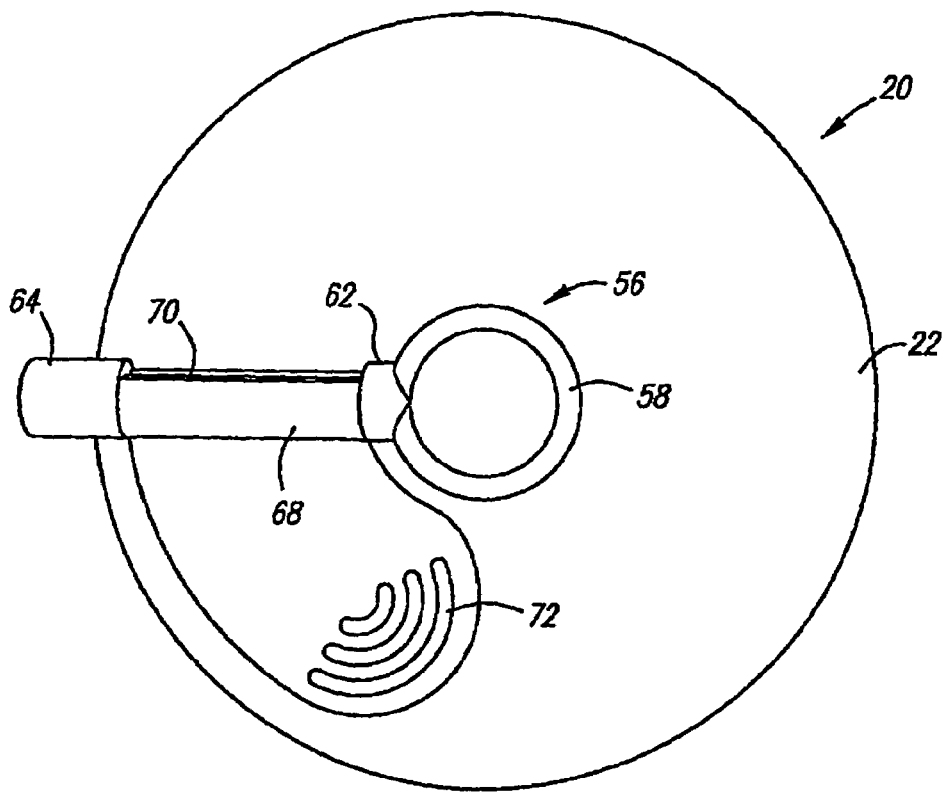
FIG. 1 is a plan view of a port assembly.

Turning in detail to the drawings, FIGS. 1 through 7 illustrate a first port assembly, generally designated 20. The port assembly 20 includes a base 22 which is shown to be frustoconical. The base may alternatively be cylindrical. Other shapes, of course, can also be employed. The base includes a mounting side 24. The mounting side may include adhesive for retention at a site on a living body. The adhesive is preferably nondrying and may or may not include a coated paper cover to be removed prior to use. A port 26 is arranged in the base 22 to be open to the other side of the base from the mounting side 24. In this embodiment, the port opens into a cavity 28 defined by a cannula mounting element 30 and a retainer element 32 which are sonically welded, press fit or cemented into the main part of the base 22.

Figure 5:
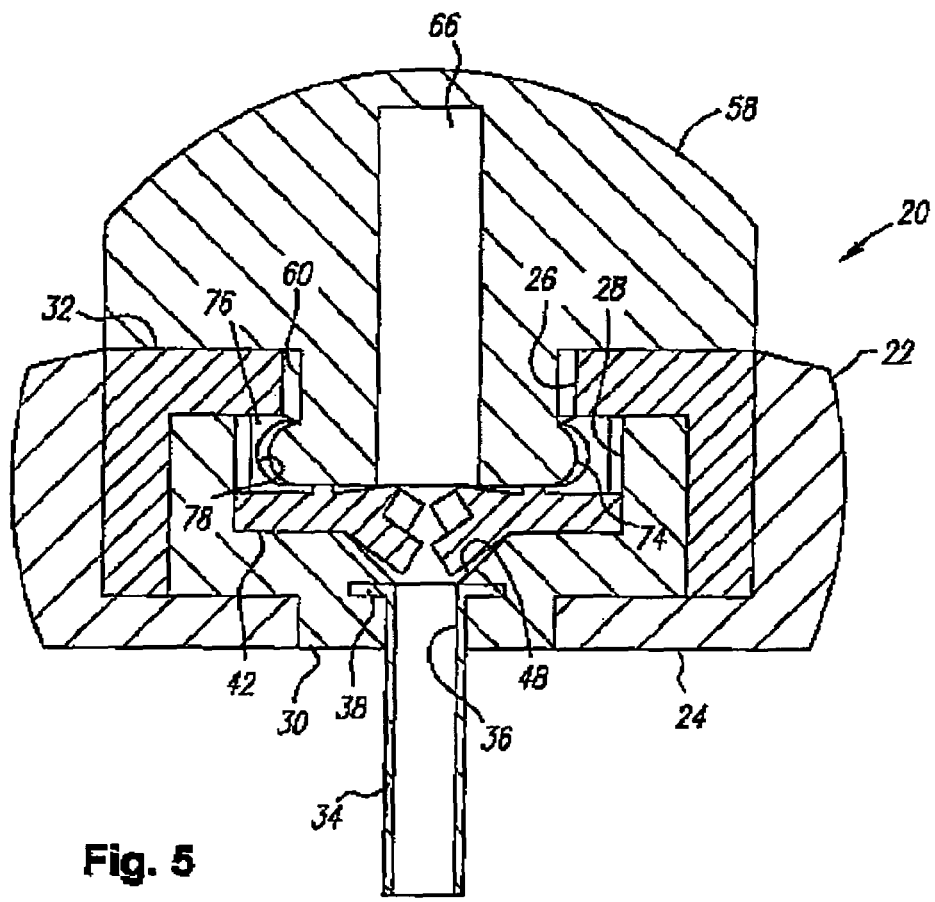
FIG. 5 is a detail view as seen in FIG. 3.

A cannula 34 extends from the base 22. In this embodiment, the cannula extends perpendicular to the mounting side 24. Other angles might be appropriately employed. The cannula mounting element 30 provides a passage 36 into which the cannula 34 is positioned. The cannula 34 has a mounting flange 38 to retain the cannula 34 from being drawn through the passage 36. The cannula 34 may be retained in the cannula mounting element 30 and a seal formed with the passage 36 through the use of adhesive, sonic welding where the materials are compatible, a press fit, or sealing elements. In the preferred embodiment, the cannula mounting element 30 insures retention of the cannula 34 by ultrasonically swaging the body of the element 30 to draw material from that element 30 over the flange 38, as best seen in FIG. 5.

The port assembly 20 further includes a resilient barrier 42. The resilient barrier 42 is preferably an elastomer. It is positioned in the cavity 28 and overlies the cannula 34. The resilient barrier 42 controls fluid communication from the port 26 to the cannula 34.

The resilient barrier 42 is illustrated in this embodiment to be a valve. The valve 42 is defined by a circular elastomeric septum 44. The septum 44 includes a slit 46 therethrough. The slit 46 is cut so that the valve remains closed when in the unstressed state. A frustoconical concavity 48 provides relief for flexure of the septum 44 downwardly to open the slit 46. As can best be seen in FIG. 6, the septum 44 includes shaped protrusions 50 to influence the distortion of the septum 44 with pressure from above. The septum 44 further includes circular beads 52 and 54. These beads provide seals for sealing contact with components on either side of the septum 44. Thus, the circular bead 54 provides sealing contact with the cannula mounting element 30 about the cannula 34 and also about the concavity 48. Thus, the resilient barrier 42 controls communication from the port 26 to the cannula 34 through pressure on the upper side thereof.

Figure 2:
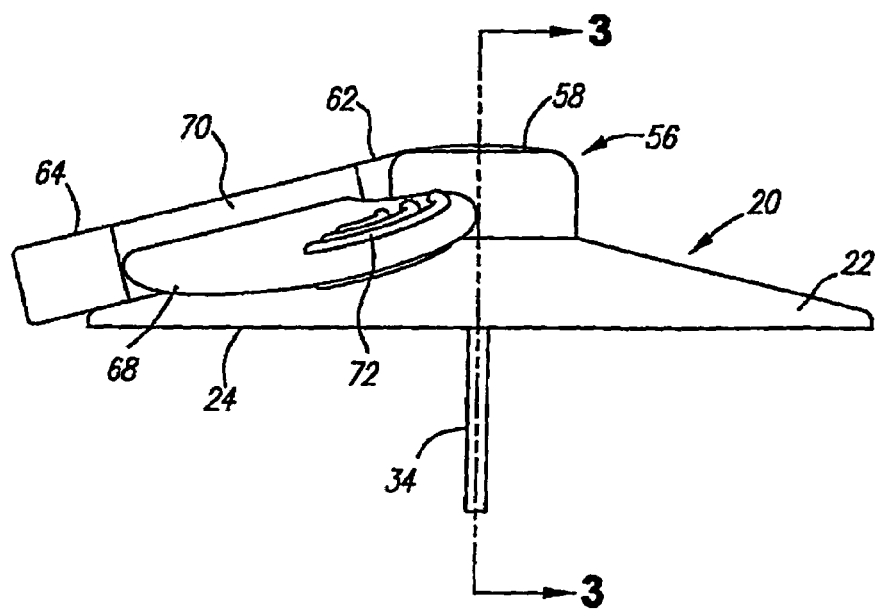
FIG. 2 is a side view of the port assembly of FIG. 1.
Figure 3:
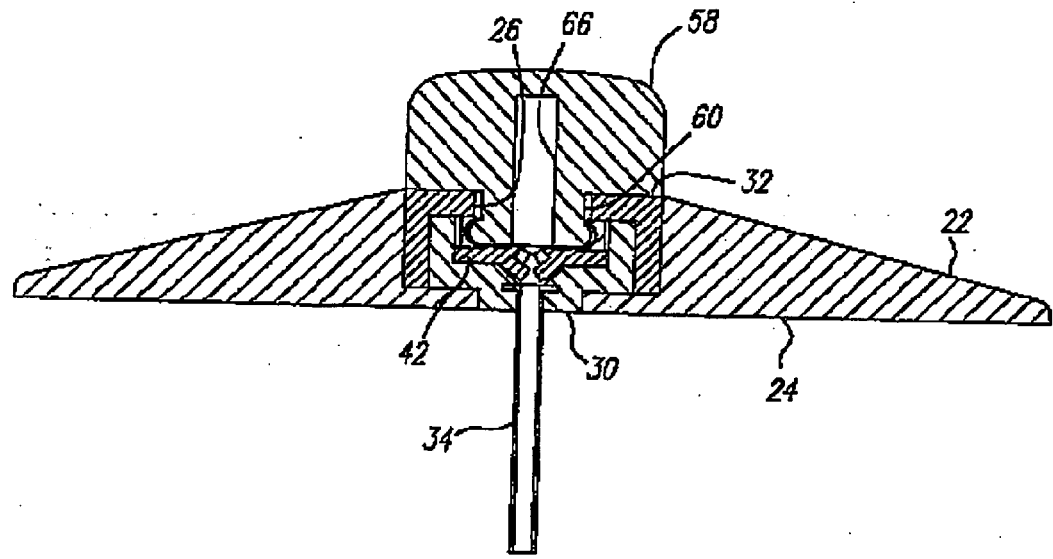
FIG. 3 is a cross-sectional view of the port assembly of FIG. 1 taken through the axis thereof along line 3—3 of FIG. 2.
Figure 4:
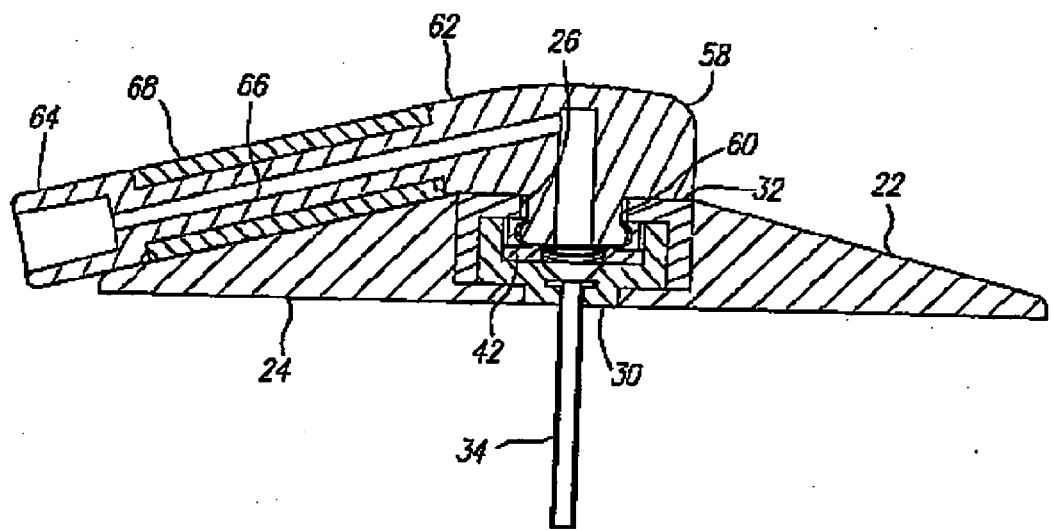
FIG. 4 is a cross-sectional view of the port assembly taken at 90° to the cross-sectional view of FIG. 3.

An access hub, generally designated 56, includes a hub 58. A connector 60 extends from the main body of the hub 58. A tube 62 extends laterally from the main body of the hub 58. A fitting 64 is located at the end of the tube 62 for receipt of an infusion tube (not shown). Other fittings may be employed to rigidly engage such tubing or other components. A passage 66 extends through the fitting 64, the tube 62 and the connector 60 to provide flow communication through the access hub 56. The tube 62 has a length of reduced outside diameter to receive a tab 68. The tab 68 is pivotally mounted about the area of reduced cross section of the tube 62. The tab 68 includes a split hub 70 for forced mounting on the tube 62. Ribs 72 on the tab 68 provide increased purchase. The tab 68 has a first position as illustrated in FIGS. 1 and 2. In a second position, the tab may be pivoted to extend more aligned with the longitudinal direction of the connector 60 for easy gripping between thumb and forefinger.

The access hub 56 is constructed such that the connector 60 can be positioned through the port 26 into the cavity 28 and fully against the resilient barrier 42, as seen in each of the relevant Figures. The bottom of the connector 60 includes a surface able to press against the shaped protrusions 50 on the opposed surface of the circular elastomeric septum 44. The protrusions 50 might alternatively or additionally be found on the end of the connector 60 but it is preferred that they be located on the septum 44 such that rotation of the access hub 56 relative to the port assembly 20 will not impact on the communication through the slit 46. The connector includes an annular surface 74 which, in cross section as illustrated in FIG. 5, is shown to provide a segment of a circle. The curved portion of the surface 74 facing toward the distal end of the connector 60 aids in the location of the access hub 56 into the port assembly 20. The more proximal portion of the annular surface 74 cooperates with a radially resilient bearing ring 76 located within the cavity 28. Together the annular surface 74 and the radially resilient bearing ring 76 define a coupling between the port assembly 20 and the access hub 56. The ring 76 is preferably split to create adequate radial resilience. The ring 76 includes an inner concave track 78 meeting with the annular surface 74. The resilience in the ring 76 and the shape of the concave track 78 cause the ring 76 to draw the connector 60 further into the cavity 28 as the ring 76 attempts to contract. This bias forces the flat end of the connector 60 against the circular bead 54 to result in sealing contact therebetween. The placement of the connector 60 is such that the circular bead 54 is located about the end of the passage 66. The annular surface 74 is small enough to fit through the port 26 and to force open the ring 76.

The port assembly 20 and access hub 56 of this first embodiment provide for the placement of the port assembly 20 in the body prior to an assembly of the port assembly 20 and the access hub 56. Once assembled, the connector 60 of the access hub 56 is biased against the septum 44, resulting in the circular beads 52 and 54 sealing against the connector 60 and the cannula mount element 30, respectively. The distal surface of the connector 60 forces the shaped protrusions 50 toward the cannula 34 to open the slit 46. Once open, the slit 46 provides communication from the passage. 66 to the cannula 34. Further, the access hub 56 can be pivoted about the centerline of the connector 60. When the access hub 56 is removed by extraction force transmitted by the tab 68, the slit 46 returns to the closed position as the force acting upon the shaped protrusion 50 is removed.

Figure 6:
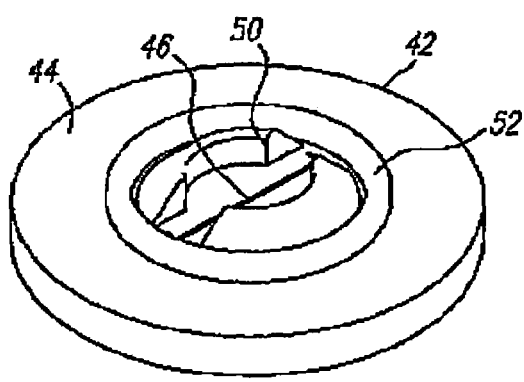
FIG. 6 is a perspective view of a resilient barrier.
Figure 7:
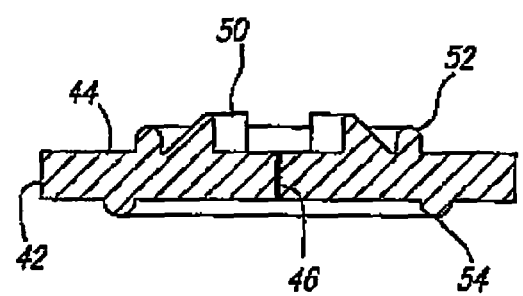
FIG. 7 is a cross-sectional view of the resilient barrier.
Figure 8:
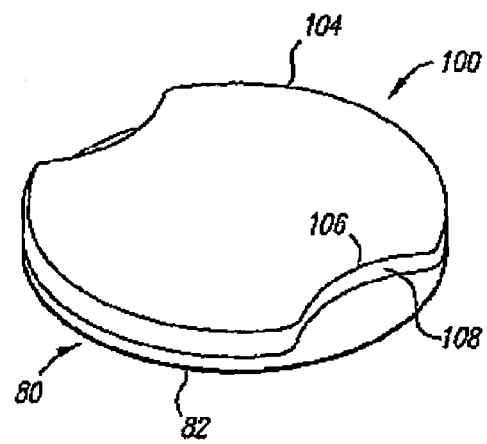
FIG. 8 is a perspective view of a second port assembly.
Figure 9:
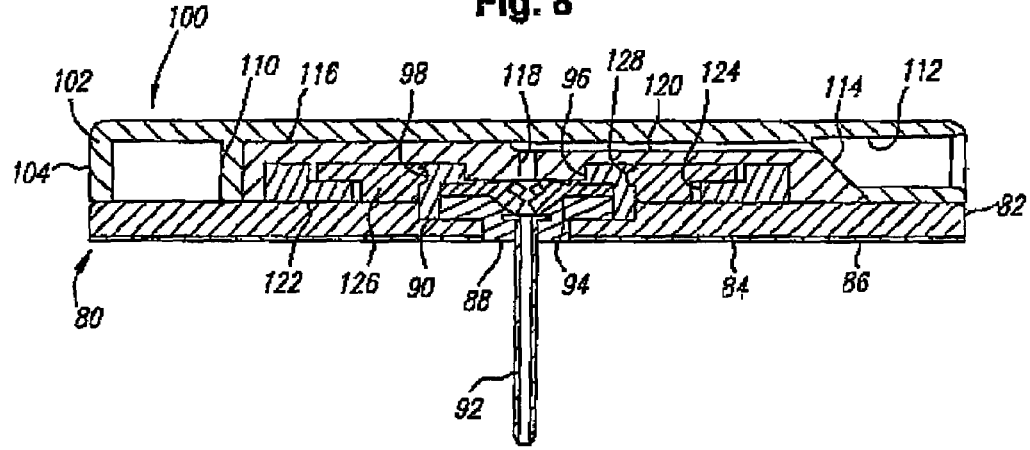
FIG. 9 is a cross-sectional view of the port assembly of FIG. 8 taken through the axis.

Another port assembly, generally designated 80, is illustrated in FIGS. 8 and 9. This port assembly 80 exhibits a flat rather than frustoconical profile. A base 82 again provides a mounting side 84 which may include adhesive 86. A cannula mounting element 88 is fixed in the base 82 and has a retainer element 90 thereabout which is also fixed in the base 82. The cannula mounting element 88 retains a cannula 92 much as in the first embodiment. Further, a resilient barrier 94 defined by the circular elastomeric septum 44 as illustrated in FIG. 6 of the first embodiment is held between the cannula mounting element 88 and the retainer element 90. The retainer element 90 defines a port 96. The retainer element 90 also defines a post about the port 96 including an annular surface 98. The surface 98 defines a concave track about the post thus defined.

An access hub generally designated 100, can be assembled with the port assembly 80. The access hub 100 includes a hub 102 having a hub circular periphery 104. This periphery 104 includes cut-outs 106 diametrically opposed with undercut sides 108. The cut-outs 106 expose the base 82 so that a pinching of the assembly with the thumb and forefinger will separate the access hub 100 from the port assembly 80.

The hub 102 provides a cylindrical cavity 110 which has one portion about the periphery thereof modified for the provision of a fitting 112. The fitting 112 again provides for infusion tubing (not shown). An inclined asymmetry 114 at the fitting 112 insures that the infusion tubing is not pushed so far into the fitting 112 that a further passageway into the access hub 100 is closed off.

An inner hub element 116 fits within the cylindrical cavity 110 and defines a connector 118 and a passage 120. The passage 120 extends from the fitting 112 to through the connector 118. The passage 120 is formed as a channel in the inner hub element 116 and closed by the hub 102. Further, the passage 120 extends through the connector 118. As with the prior embodiment, the connector 118 is insertable to the resilient barrier 94, operating in the same way as the first embodiment in the influence on opening the valve mechanism associated therewith.

A retainer 122 is fixed to the inner web element 116. The retainer 122 is contemplated to extend fully about the inner cavity 124 defined within the inner hub element 116. The inner hub element 116 and the retainer 122 capture a radially resilient bearing ring 126 within the inner cavity 124. This bearing ring 126 is preferably split and includes a convex annular bead 128 which cooperates with the annular surface 98 to define a coupling between the port assembly 80 and the access hub 100. Albeit the location of the elements are inverted, the ring 126 acts in a similar way to that of the first embodiment in that it is sized and arranged to force the connector 118 into sealing contact with the resilient barrier 94. Again, one of the end surfaces of the connector 118 and the resilient barrier 94 includes shaped protrusions to cause opening of the valve upon placement of the connector 118 in the port 96.

Figure 10:
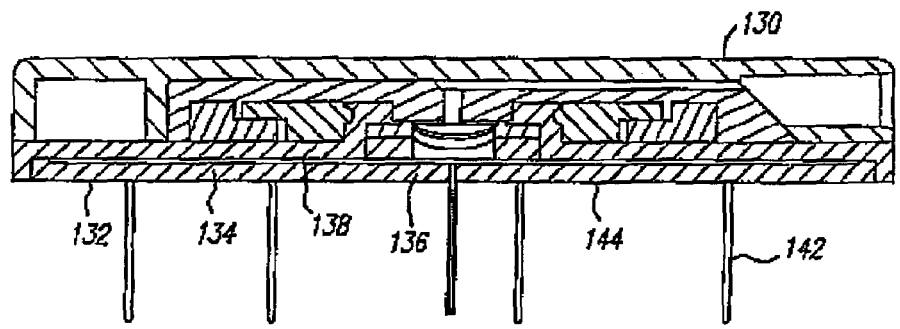
FIG. 10 is a cross-sectional view of a third port assembly also taken through the axis of the assembly.

A further port is illustrated in FIG. 10. The access hub 130 is identical to that of the embodiment of FIGS. 8 and 9. Further, FIG. 8 applies equally to the embodiments of FIG. 9 and FIG. 10. The port assembly 132 includes a base 134 which is defined by a cannula mounting element 136 and a disk 138 having a cylindrical flange about the outer periphery thereof. Together the mounting element 136 and disk 138 provide a flow area therebetween which is able to reach a plurality of cannulas 142 extending from the mounting surface 144. These cannulas 142 are rigid but are contemplated to be very short so as to provide dispersed infusion into living tissue or multi-sensor diagnostic access. The cannulas are rigidly fixed within the cannula mounting element 136. Further, the cannula mounting element 136 provides a broader opening which communicates with the flow area between the plate 136 and the disk 138 for adequate distribution of infusion fluids thereabout.

Figure 13:
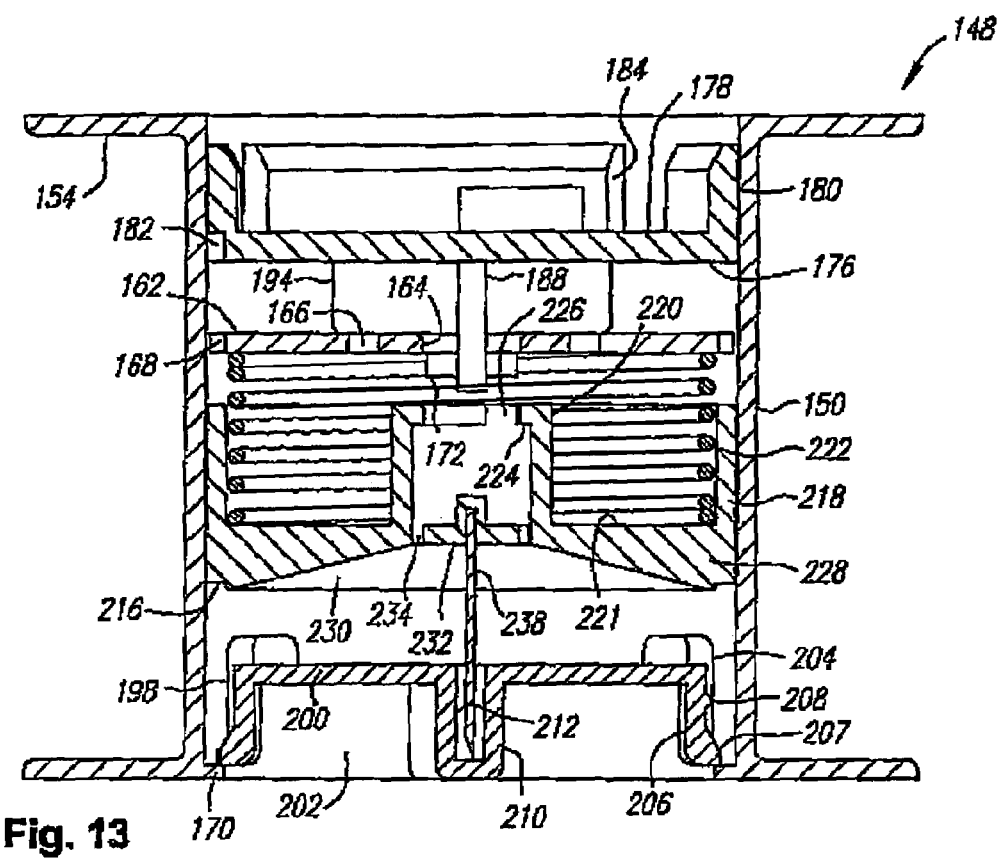
FIG. 13 is a cross-sectional view of the port inserter of FIG. 12 with the inserter discharged and closed, the view being at 90° to FIG. 12.
Figure 14:
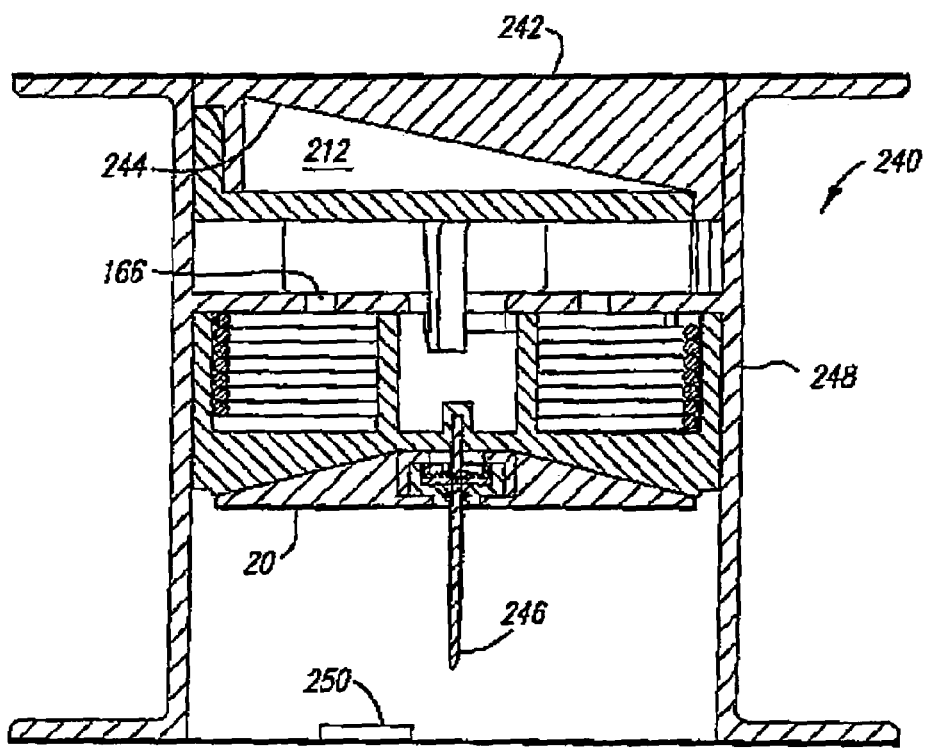
FIG. 14 is a cross-sectional view of a second port inserter taken through the axis of the inserter.
Figure 16:
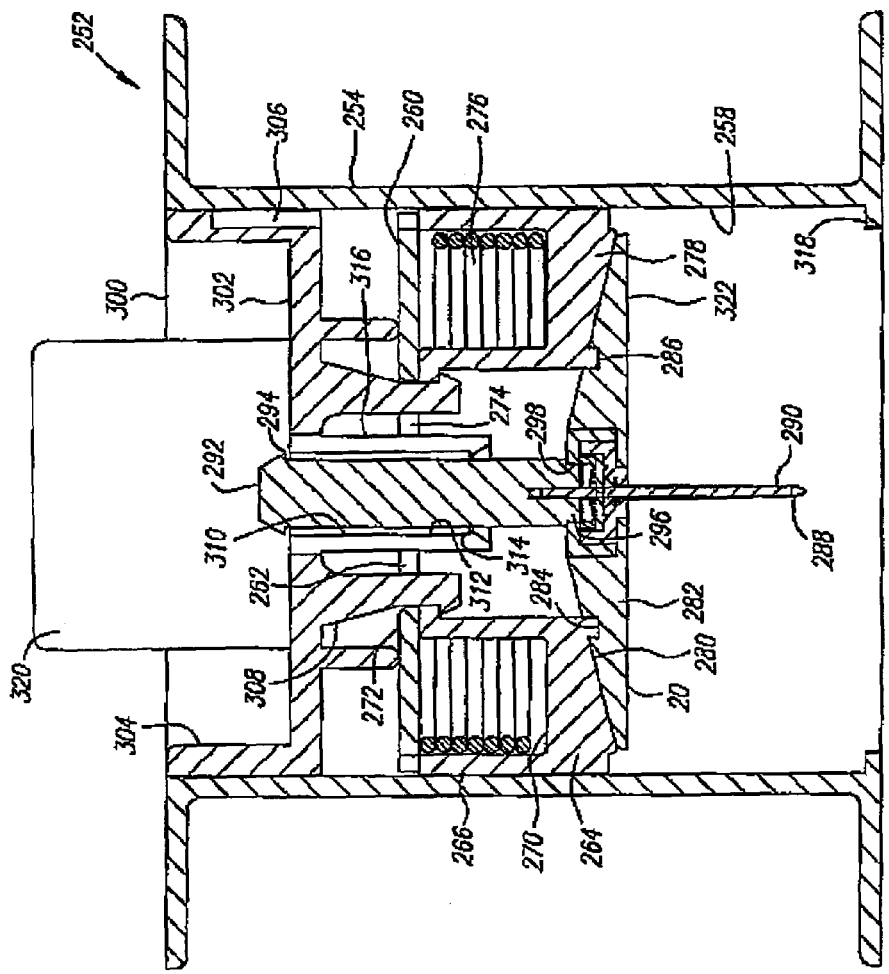
FIG. 16 is a cross-sectional view taken along an axis of the port inserter of FIG. 15.
Figure 15:
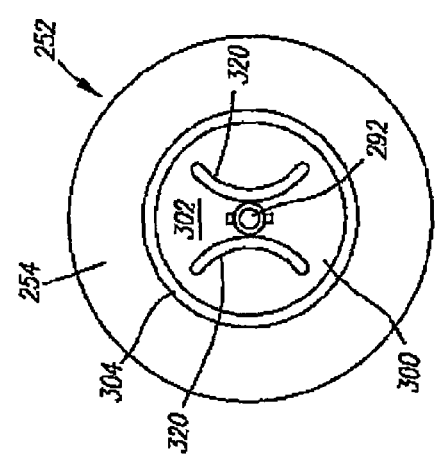
FIG. 15 is a plan view of a third port inserter.
Figure 17:
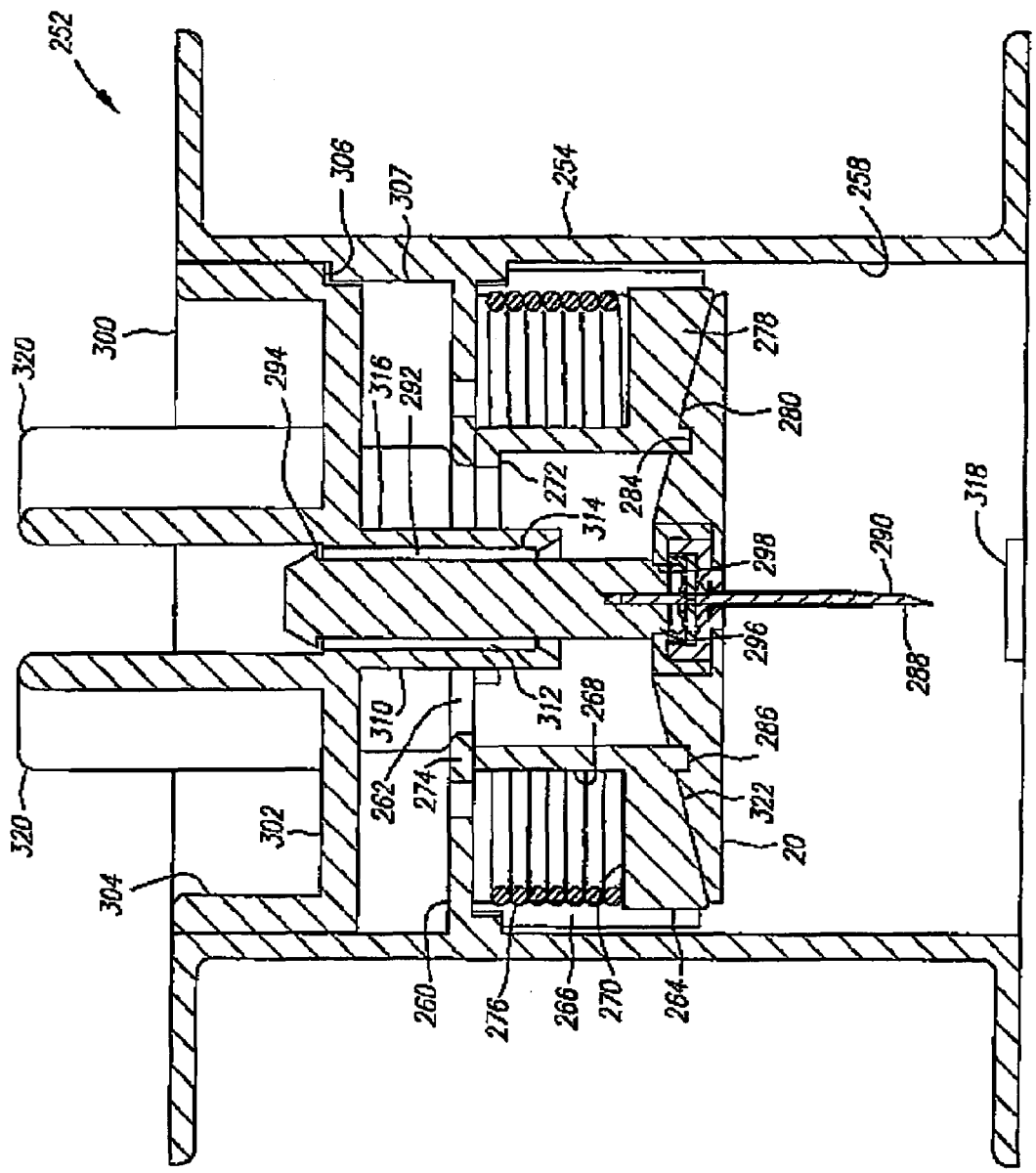
FIG. 17 is a cross-sectional view taken along an axis of the port inserter of FIG. 15 at 90° to the view of FIG. 16.
Figure 19:
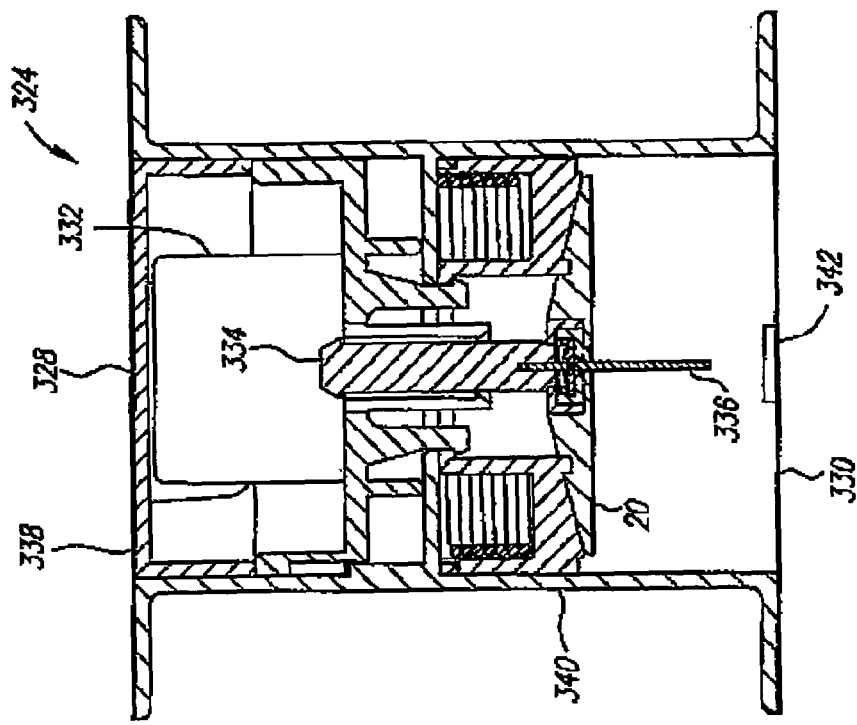
FIG. 19 is a cross-sectional view taken along an axis of the port inserter of FIG. 18 at 90° to the view of FIG. 18.
Figure 18:
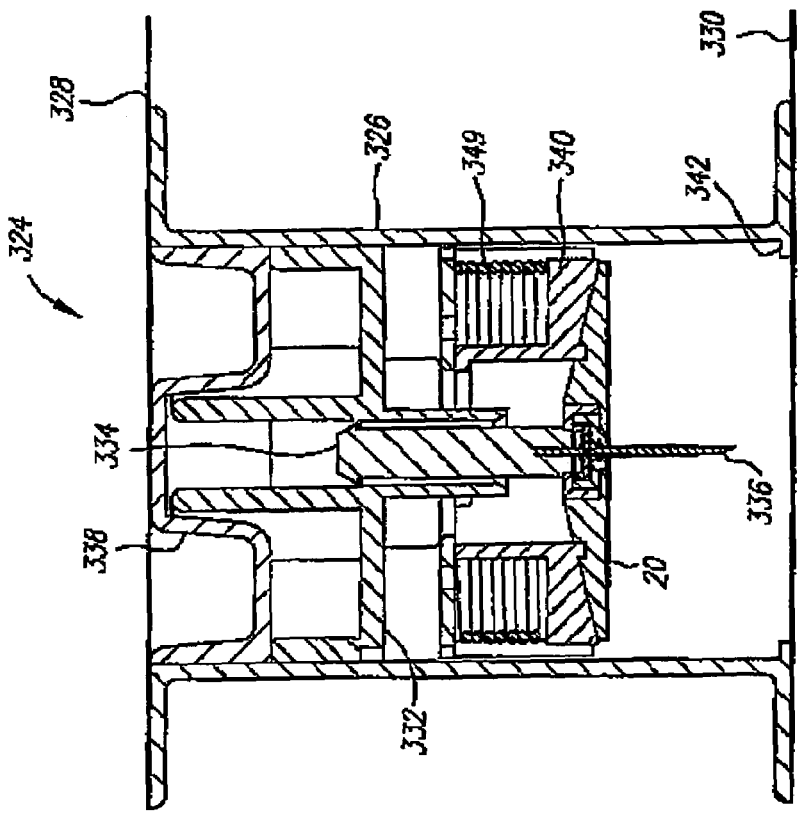
FIG. 18 is a cross-sectional view taken along an axis of a fourth port inserter.

FIGS. 11 through 19 provide inserter embodiments. These embodiments are shown to mate with the port assembly 20. Through slight modification of the seat within which the port assembly is positioned, the embodiments of FIGS. 8 through 10 might also be accommodated. The first two embodiments, FIGS. 11 through 13 and 14 are advantageously configured for disposable use. The embodiment of FIGS. 15 through 17 is most advantageously reusable. Finally, the embodiment of FIGS. 18 and 19 is configured for reusable or disposable use.

In the embodiment of FIGS. 11 through 13, the inserter, generally designated 148, is shown to include a housing assembly including a housing 150. The housing 150 is conveniently cylindrical with a bore 152 and outwardly extending flanges 154 to define circular attachment surfaces at either end of the bore 152. First and second closures 156 and 158 can be retained on the flanges 154. These closures 156 and 158 include a tab 160 such that they are conveniently removably mounted across the bore 152 with adhesive. The closures 156 and 158 are preferably peal-off sheets commonly employed for sterile closures.

The housing 150 further includes a mount 162 extending across the bore 152 and integrally formed with the housing 150. The mount 162 is in the form of a plate perpendicular to the axis of the bore 152. A central hole 164 is provided through the mount 162 to receive a latch discussed below. Two holes 166 elongate in cross section extend to either side of the central hole 164. These holes are parallel and are located symmetrically about the center axis of the housing. Certain additional holes 168 are provided through the mount 162 for molding purposes.

The housing 150 further includes stops 170 extending inwardly in the bore 152 and conveniently being diametrically opposed to one another. The holes 168 for molding purposes are aligned with the stops 170 such that molding of the stops 170 is facilitated. Indexing tabs 172 are also diametrically placed to one side of the mount 162 and are also formed as part of the inner wall of the housing 150. On the other side of the mount 162, a key 174 extends into the bore 152 and from the mount 162.

A latch 176 is positioned to one side of the mount 162. The latch includes a plate 178 extending substantially across the bore 152 of the housing 150. Additionally, the latch 176 includes upwardly extending walls 180 forming segments of a cylinder. One of these segments of the walls 180 includes a keyway 182 which receives the key 174. The keyway 182 has a substantial portion having a first height to receive the key 174 with the latch 176 axially positioned as shown in FIG. 12. At one point, the keyway 182 is of increased depth parallel to the centerline of the housing 150 which allows the latch 176 to move toward the mount 162. The walls 180 have three gaps 184 therebetween. One of the walls 180 also includes an undercut section 186.

Hooks 188 extend in the opposite direction of the walls 180 from the plate 178. These hooks 188 include outwardly extending barbs 190 which extend through the central hole 164 in the mount 162. The barbs 190 have inclined surfaces 192 such that they can be forced into the central hole 164 with the hooks 188 exhibiting some resilience. The barbs 190 on the hooks 188 are spaced such that once inserted through the central hole 164, they will engage the rim of the hole 164 regardless of the angular orientation such that the latch 176 is permanently captured by the mount 162.

Setoffs 194 extend in the same direction from the plate 178 as the hooks 188. These setoffs 194 are straight and parallel to one another and equally displaced from the axis of the housing. The setoffs 194 match the parallel holes 166 so that the latch 176 may be forced closer to the mount 162. However, the hooks 188 also each have an inclined surface facing outwardly which inhibits substantial movement of the latch 176 toward the mount 162 from the position a shown in FIG. 12. In position for use, the latch 176 is oriented such that the standoffs 194 are not aligned with the parallel holes 166 such that the latch 176 is held axially within the bore 152 of the housing 150. During assembly of the inserter might the latch be angularly rotated to match the setoffs 194 with the parallel holes 166 to insure that assembly can be accomplished.

A cover 198 is arranged with the latch 176. The cover also includes a plate 200 which generally lies against the plate 178 of the latch 176. A cylindrical wall 202 extends upwardly from the plate 200. This wall 202 includes three blocks 204 which extend radially outwardly from the wall 202. These blocks 204 engage the gaps 184 in the upwardly extending walls 180 of the latch 176. Consequently, rotation of the cover 198 will result in rotation of the latch 176 with the two components in mating relationship.

The cover also includes two fingers 206 diametrically opposed and spaced in cutout portions of the cylindrical wall 202. One of these fingers 206 includes a rounded circumferentially extending bar 208 which engages the undercut section 186 in one of the upwardly extending wall segments 180. The bar 208 provides some retention of the cover 198 but allows it to be removable with a small amount of force. The two opposed fingers 206 are slightly shorter than the full extent of the upstanding wall 202 and have inclined surfaces 207. The fingers 206 are somewhat resilient and can move radially inwardly because of the cuts to either side of the fingers 206 in the cylindrical wall 202.

Centrally located in the plate 200, an integral channel 210 extends across the cover 198. This integral channel 210 forms a chamber 212 open toward the latch 176.

The structure of the cover 198 is such that it can be extracted from association with the latch 176 and pulled from the housing 150. The cover 198 may then be turned over and forced into the other end of the housing 150 within the bore 152 as seen in FIG. 13. The fingers 206 resiliently ride over the diametrically opposed stops 170 across the inclined surfaces 207 and lock on the upper surface of the fingers 206.

The cylindrical wall 202 has an additional rim 214 about its circumference to fit closely within the bore 152 of the housing 150 in this position. As such, the lower end of the bore 152 is closed by the cover 198 after use. The upper end of the bore 152 remains substantially closed by the plate 178 of the latch 176.

A port driver, generally designated 216, is slidably mounted within the bore 152 of the housing 150. The port driver 216 includes a cylindrical outer wall 218 which slides within the bore 152. The cylindrical outer wall 218 includes two gaps (not shown) diametrically opposed. These gaps mate with the indexing tabs 172 which extend from the mount 162. These gaps also provide clearance to allow the port driver 216 to be mounted in the housing 150 across the stops 170. The gaps extend fully through the port driver 216 and allow for air flow as the driver 216 moves through the housing 150. A cylindrical inner wall 220 defines an annular spring cavity 221 for receiving a coil spring 222. The cylindrical inner wall 220 includes an inwardly extending flange 224 which includes notches 226 diametrically opposed where there is no inwardly extending flange 224. As such, the hooks 188 which extend through the central hole 164 further extend into the cylindrical inner wall 220 and engage the inwardly extending flange 224 unless aligned with the notches 226.

A plate 228 extends across the port driver 216 from which the cylindrical walls 218 and 220 extend to form the annular spring cavity 221. This plate 228 provides a seat 230 which is shown in FIGS. 12 and 13 to be conically formed to accommodate the first embodiment port assembly 20. The seat 230 may easily be formed to accommodate the port assemblies 80 and 132. In this disposable embodiment, the seat 230 does not in any way restrain the port assembly 20 from moving away from the seat 230. The plate 228 does extend outwardly to the wall of the bore 152 such that the stops 170 will engage the plate 228 as it moves to the end of the housing 150.

The plate 228 includes a central portion 232 having holes 234 facilitating the molding process of the flanges 224. The holes are directly aligned with the inwardly extending flange 224 to that end. A socket 236 is centrally located within the central portion 232. This socket 236 is sized to receive a needle which may be forcefully fit within the socket 236 or permanently retained there by a bonding agent. In either circumstance, the socket is designed to rigidly and permanently fix a needle employed as a cannula insertion member.

A cannula insertion member 238 in the form of a sharp needle is permanently affixed within the socket 236. This needle 238 extends downwardly through the port assembly 20 and through the cannula 34 associated therewith. The cannula 34 is fit snugly about the needle 238 such that friction does exist between the cannula 34 and the needle 238. The retention force thus provided maintains the port assembly 20 in place prior to application. The adhesive on the mounting side 24 is formulated to have a greater separation force than the retention force between the cannula 34 and the needle 238. Further, the base 22 is sized to miss these stops 170.

In operation, the inserter 148 is assembled by pressing the latch 176 into position with the hooks 188 extending through the central hole 164. The cover 198 is also positioned on the latch 176 and forced into place. The latch may be oriented such that the parallel setoffs 194 engage the parallel holes 166 so that the latch 176 may be forced further into the bore 152 to insure engagement with the port driver 216. The coil spring 222 is placed between the mount 162 and the port driver 216 in the annular spring cavity 221. The port driver is aligned with the housing 150 so that the gaps match up with the stops 170. With the spring operatively positioned between the mount 162 and the port driver 216, the port driver is forced upwardly and angularly displaced until the hooks 188 engage the inwardly extending flange 224.

The cannula insertion member 238 may originally be part of the inserter 148 by location in the socket 236 with a bonding agent or through forced interference fit. Alternatively, the cannula insertion member 238 may first be temporarily assembled with the port assembly 20 through the cannula 34 and then associated with the port driver 216 as the port assembly 20 is positioned. Ultimately, the cannula insertion member 238 becomes a fixed part of the port driver 216.

The closures 156 and 158 are then positioned and fixed on the ends of the housing 150 and the device sterilized. Depending on the method of sterilization, the device is sterilized after placement of the closures 156 and 158.

In use, the closures 156 and 158 are removed by pulling on the tabs 160. The inserter 148 is then placed on the body site. The cover 198 is then rotated until the hooks 188 meet the notches 226 in the inwardly extending flange 224, releasing the port driver 216. The spring 222 propels the port driver 216 forwardly to the end of the housing 150 where it engages the stops 170. The port assembly 20 is advanced with the port driver 216 until the adhesive contacts the surface of the body. In doing so, the cannula insertion member 238 is rapidly advanced into the body along with the supported cannula 34. Once placed, the housing 150 is retracted from the body retaining the port driver 216 including the cannula insertion member 238. The resilient barrier 42 prevents flow from the body through the cannula 34. With the inserter 148 removed, the cover 198 is pulled from the end of the housing 150 and placed on the other end thereof to engage the fingers 206 with the stops 170. The container 212 defined by the channel 210 receives the cannula insertion member 238 to cover the sharp and close the container.

With the port assembly 20 in place and the inserter 148 removed, an access hub 56 can then be placed. As the connector 60 is inserted into the port 26 of the port assembly 20, the end surface of the connector 60 extends against the shaped protrusions 50 of the resilient barrier 42. The connector 60 does not extend through the slit 46 but opens the valve through its positioning in the cavity 28. The coupling mechanism including the radially resilient bearing ring 76 and the annular surface 74 is engaged; and the connector 60 is pressed against the circular bead 52. The access hub 56 is then movable in the port assembly 20 and can be pivoted to best advantage for the associated infusion tubing. Removal of the access hub 56, in this embodiment by the tab 68, will withdraw the connector 60 and allow the slit 46 to again close in the resilient barrier 42.

Turning to the port driver 240 illustrated in FIG. 14, the mechanism is substantially identical to that of the embodiment of FIGS. 11 through 13. However, the cover 242 is differently configured principally with a channel 244 having a container 212 which is askew to bend the cannula insertion member 246 to the side as the cover 242 is placed on the driver end of the housing 248. Stops 250 again engage the cover 242 to hold it in place.

Turning to the inserter embodiment of FIGS. 15 through 17, a reusable inserter, generally designated 252, is disclosed. The inserter includes a housing 254 which is substantially identical to prior housings. The bore 258 includes a mount 260 extending across the housing 254 as previously described. However, the central hole 262 is increased in size for placement considerations.

The port driver 264 includes a cylindrical outer wall 266 and a cylindrical inner wall 268 defining an annular spring cavity 270. Inwardly extending flanges 272 are located at the end of the cylindrical inner wall 268 most adjacent the mount 260. Again, notches 274 in the inwardly extending flanges 272 are arranged diametrically. A coil spring 276 is located within the annular spring cavity 270. In this embodiment, the center area of the port driver 264 is open. An annular plate 278 closes the bottom of the annular spring cavity 270 and defines a seat for a port assembly 20. In this embodiment, the base 282 of the port assembly 20 includes a circular channel 284. The seat 280 of the annular plate 278 includes a retainer 286 in the form of a circular ring which engages a circular channel 284 with minimal release force generated by a minimal interference fit to retain the port assembly 20 in place prior to insertion.

The cannula insertion member 288 includes a sharpened needle 290 and a needle hub 292. The needle 290 is permanently retained within the needle hub 292. The needle hub 292 includes an engagement shoulder 294 at its distal end and a plug 296 that fits within the port 298 of the port assembly 20.

A latch 300 is located to the other side of the mount 260 from the port driver 264. The latch includes a plate 302 extending across the bore 258 of the housing 254. A cylindrical wall 304 extends along the bore 258. A keyway 306 is found in the cylindrical wall 304 to receive a key 307 associated with the housing 254. Hooks 308 are provided as in prior embodiments but are spaced further apart to allow for the needle hub 292.

A socket 310 is centrally located in the plate 302 of the latch 300. This socket 310 releaseably retains the needle hub 292 which is otherwise slidable within the socket 310. The socket 310 includes a passageway 312 which is open at the end toward the port assembly seat 280. A shoulder 314 is presented at the end of the passageway 312 to encounter and retain the engagement shoulder 294 of the needle hub 292. The socket 310 is also split diametrically along its length to form two socket elements 316. The length of the socket 310 is such that, in combination with the needle hub 292, the engagement shoulder 294 and the shoulder 314 do not stop insertion of the cannula insertion member until the needle 290 has penetrated the body to the point that the associated cannula 34 will not extend beyond the needle 290. The arrangement is designed to stop the cannula insertion member 288 before the port driver 264 has traveled fully to the stop 318 located in the bore 258 of the housing 254.

With the inserter 252 having been actuated by rotation of the latch 300 and the port assembly 20 placed, the inserter 252 can be withdrawn along with the cannula insertion member 288 as a component of the inserter 252. Once withdrawn, the cannula insertion member 288 can be released from the reusable inserter 252. The plate 302 defines a slightly flexible web across the bore 258 of the housing 254. Two opposed levers 320 extend upwardly from that web 302. These levers are aligned with the socket elements 316 defining the socket 310. By pinching the levers 320 together, the socket elements 316 splay apart and release the needle hub 292. A new cannula insertion member 288 can then be positioned in the inserter 252 by forcing it past the shoulder 314. This may be accomplished with or without the port assembly 20.

With the reusable inserter 252, the device may be prepared by positioning the cannula insertion member 288 in the port assembly 20. The cannula insertion member 288 is then engaged with the socket 310 by forcing the needle hub 292 through the shoulder 314 on the socket elements 316. These levers 320 may be pinched together to facilitate this assembly. The port assembly 20 is then forced against the port driver 264 to place the port assembly 20 in the seat 280 with the circular channel 284 and the circular ring 286 engaged with slight interference. Where the port assembly has exposed adhesive on the mounting side 322, it is advantageous that the port driver 264 is forced into engagement with the latch 300 before placement of the port assembly 20. Once prepared, the inserter 252 may be placed at the site and the levers 320 turned to rotate the latch 300 such that the hooks 308 meet the notches 274 and release the port driver 264. The inserter 252 is then withdrawn, retaining the cannula insertion member 288 as part of the inserter assembly. The port assembly 20 remains at the site with the cannula 34 extending into the living body. An access hub 56 is then positioned with the connector 60 in the port 26. Force is applied to engage the coupling between the two such that the access hub 56 is then movably retained within the port assembly 20. The system is then ready for delivery of therapeutic agents or diagnostic agents through the cannula into the living tissue. The access hub 56 may be withdrawn through force exerted on the tab 68, or by pinching the access hub in the second or third embodiments. The valve of the resilient barrier 42 responds appropriately by sealing the pathway when the access hub 56 is not in place and opening the pathway when it is.

A further port inserter as illustrated in FIGS. 18 and 19, generally designated 324, combines a number of features of the prior port inserters. The device may come fully sealed and sterile. Further, the port inserter 324 contemplates the intended release of the needle after use or the enclosure of that needle with the inserter for discard. A cylindrical housing 326, as generally described in preceding embodiments, includes an extended length to accommodate closure elements 328 and 330. A latch 332 operates identically to that in the prior embodiment of FIGS. 15 through 17 and cooperates with a needle hub 334 and needle 336 in a like manner. The extended portion of the housing 326 encloses the levers of the latch 332 and receives a cover 338. This cover is constructed so that it may be forced against the driver 340 from the bottom to enclose the needle 336 and lock the cover over the stops 342. The driver 340 is the same as that of prior embodiments and is driven by a spring 344 in like manner. Likewise a port 20 also is as in prior embodiments.

Thus, improved ports and inserters therefor have been described. While embodiments and applications of this invention have been shown and described, it would be apparent to those skilled in the art that many more modifications are possible without departing from the inventive concepts herein. The invention, therefore is not to be restricted except in the spirit of the appended claims.

What is claimed is:

1. A system for delivery of therapeutic and/or diagnostic agents into a living body, comprising
   a. a port assembly including
      (1) a base having a mounting side,
      (2) a port opening away from the mounting side,
      (3) a cannula extending from the mounting side and
      (4) a resilient barrier with a hole therethrough between the port and the cannula controlling communication between the port and the cannula;
   b. an access hub including
      (1) a connector positionable in the port at the resilient barrier,
   the hole in the resilient barrier being closed with the connector displaced from being positioned in the port and open with the connector fully positioned in the port.

2. The system of claim 1, the access hub being engageable with the port assembly to resist separation from the port assembly and rotatable relative to the port assembly with the connector fully positioned in the port.

3. The system of claim 1, the hole being a slit.

4. The system of claim 1, there being only one cannula.

5. A system for delivery of therapeutic and/or diagnostic agents into a living body comprising
   a. a port assembly including
      (1) a base having a mounting side,
      (2) a port opening away from the mounting side,
      (3) a cannula extending from the mounting side and
      (4) a resilient barrier with a slit therethrough between the port and the cannula controlling communication between the port and the cannula;
   b. an access hub including
      (1) a connector positionable in the port at the resilient barrier,
   the hole in the resilient barrier being closed with the connector displaced from being positioned in the port and open with the connector fully positioned in the port, the resilient barrier having
      (a) at least one protrusion aside the slit in interference with the connector with the connector fully positioned in the port.

6. A system for delivery of therapeutic and/or diagnostic agents into a living body, comprising
   a. a port assembly including
      (1) a base having a mounting side,
      (2) a port opening away from the mounting side,
      (3) a cannula extending from the mounting side and
      (4) a resilient barrier with a hole therethrough between the port and the cannula controlling communication between the port and the cannula;
   b. an access hub including
      (1) a connector positionable in the port at the resilient barrier,
   the hole in the resilient barrier being closed with the connector displaced from being positioned in the port and open with the connector fully positioned in the port, the connector having
      (a) a passageway therethrough aligned with the hole, the resilient barrier having
      (a) a circular bead about the hole in sealing interference with the connector with the connector fully positioned in the port.

7. A system for delivery of therapeutic and/or diagnostic agents into a living body, comprising
   a. a port assembly including
      (1) a base having a mounting side,
      (2) a port opening away from the mounting side,
      (3) a cannula extending from the mounting side and
      (4) a resilient barrier with a hole therethrough between the port and the cannula controlling communication between the port and the cannula;
   b. an access hub including
      (1) a connector positionable in the port at the resilient barrier,
   the hole in the resilient barrier being closed with the connector displaced from being positioned in the port and open with the connector fully positioned in the port, the hole being a slit,
   the resilient barrier having
      (a) at least on protrusion aside the slit in interference with the connector with the connector fully positioned in the port,
   the connector having
      (a) a passageway therethrough aligned with the slit, the resilient barrier having
      (a) a circular bead about the slit in sealing interference with the connector with the connector fully positioned in the port,
   the port assembly further including
      (5) a resilient element in the port biasing the connector toward the resilient barrier with the connector fully positioned in the port.

* * * * *